United States Patent
Parrigan

(10) Patent No.: US 6,855,313 B1
(45) Date of Patent: Feb. 15, 2005

(54) ANIMAL ATTRACTANT

(76) Inventor: Gary Parrigan, 96 E. Smiley Ave., Shelby, OH (US) 44875

(*) Notice: Subject to any disclaimer, the term of this patent is extended or adjusted under 35 U.S.C. 154(b) by 0 days.

(21) Appl. No.: 10/404,168

(22) Filed: Apr. 1, 2003

Related U.S. Application Data

(60) Provisional application No. 60/370,550, filed on Apr. 5, 2002.

(51) Int. Cl.[7] ............................................. A01N 25/02
(52) U.S. Cl. ..................... 424/84; 424/545; 424/719; 424/721
(58) Field of Search ..................... 424/405, 84, 719, 424/721, 545

(56) References Cited

U.S. PATENT DOCUMENTS 6,030,608 A * 2/2000 Hoyes et al. ............... 424/76.1

OTHER PUBLICATIONS

Fratzke et al. Outdoor Life v1/96 No. 3, p 34 9/95.*
Levy Do–it–yourselFer Buffalonews, Sep. 30, 2001.*
Elliott Help is Here, Buffalo News, Oct. 8, 2000.*
Golden Eagle, pp. 1, 11, Mar. 1987.*
Samuel Outdoor Life 204#3, Oct. 1999.*

* cited by examiner

Primary Examiner—Neil S. Levy
(74) Attorney, Agent, or Firm—Jerry Semer

(57) ABSTRACT

The invention is basically an animal attractant that is made from human urine and animal urine. The attractant consists of a mixture of 14 to 15 parts male human urine 1 to 2 parts animal urine. The human urine is aged for two to three days. In the preferred embodiment the invention is a deer attractant. The attractant is a mixture of 14 to 15 parts human urine and 1 to 2 part deer urine. The human urine could be male, female or female during menstruation human urine. The deer urine can be doe urine, doe urine in estrous, or buck urine, both natural and synthetic. From experiments done by the inventor he found that male human urine mixed with synthetic buck urine worked best.

20 Claims, 2 Drawing Sheets

ANIMAL ATTRACTANT

This application claims the benefit of Provisional application Ser. No. 60/370,550, filed Apr. 5, 2002.

FIELD OF THE INVENTION

This invention relates to the field of animal attractants and more particularly to scents that attract deer.

BACKGROUND OF THE INVENTION

Man has for many years been attempting to find easier ways to hunt. When hunting your first objective is to find your quarry. Men, of course, have used several different methods to attempt to find his quarry. Some hunter actually studying the habits of the animals so that they can guess where the quarry would be. Other wonder around hoping they will come across the game. The easiest way to find one's quarry however is to attract the quarry. This can be done by setting out different scents. Theses scents could be relate to mating, territory and food.

The applicant has tried different deer attractants on the market over 30 years of deer hunting. He has found that the only way for the attractants to be effective is to have large quantities of the attractant around. This, of course, is very, very expensive.

The most common scent to attract animals is urine. Present think is to attract an animal one uses that animal's urine. The applicant wondered if urine from other animals like humans would also attract animals. The applicant realized that the most cost effective urine he could come by is human urine. Thus, he decided to try human urine as a base. He made several tests to using male, female and female during menstruation human urine mixed with doe urine, doe urine in estrous, and buck urine, both natural and synthetic. In these tests the applicant found that human male urine mixed with synthetic dominant buck urine was the best combination.

Making further tests he found that a combination of 14 to 15 ounces of human male urine with one or two ounces of synthetic dominant buck urine was the most effective at attracting male deer. Thus, one of the objectives of this invention is to find a scent that effectively attracts deer and other animals, however, is inexpensive. Since the cost of obtaining human urine is almost free, the hunter can use a great deal more of the scenting material to attract the deer. This makes the system much more cost effective.

The applicant objective is to create an attractant that uses human urine with animal urine, either natural or synthetic to enable hunters to put out large quantities of attractant which intensifies the odor at a very low cost and dramatically increase the hunter's chances for success.

SUMMARY OF THE INVENTION

The invention is basically an animal attractant that is made from human urine and animal urine. The attractant consists of a mixture of 14 to 15 parts male human urine and 1 to 2 parts animal urine. The human urine is aged for two to three days. In the preferred embodiment the invention is a deer attractant. The attractant is a mixture of 14 to 15 parts human urine and 1 to 2 parts deer urine. The human urine could be male, female or female during menstruation human urine. The deer urine can be doe urine, doe urine in estrous, or buck urine, both natural and synthetic. From experiments done by the inventor he found that male human urine mixed with synthetic buck urine worked best.

DETAILED DESCRIPTION OF THE PREFERRED EMBODIMENT

Figure 1:
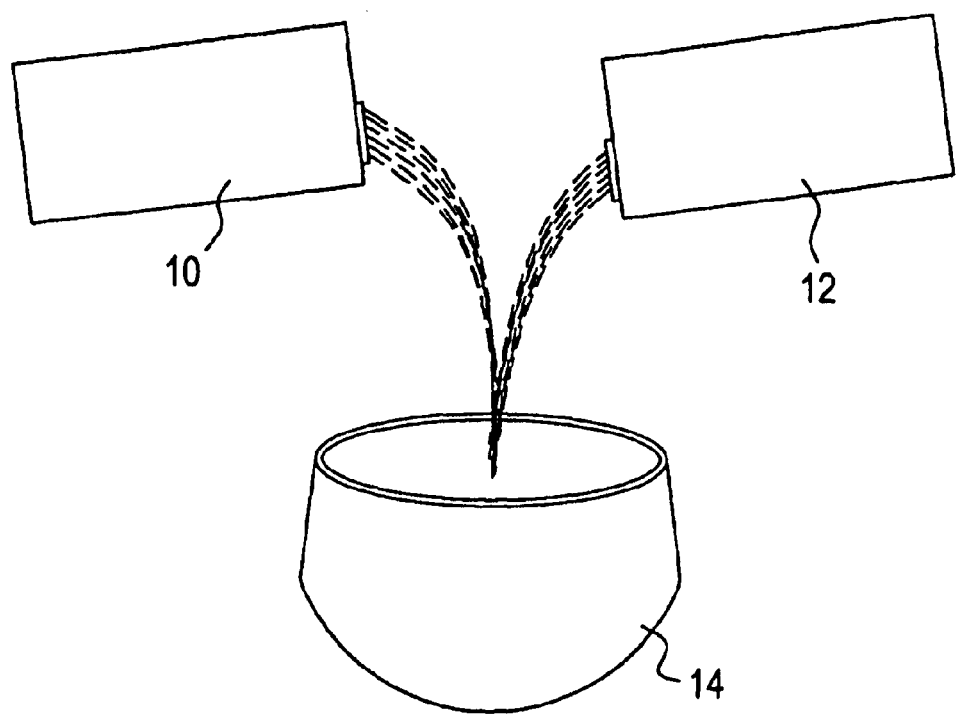
FIG. 1 shows the mixing to the two ingredients that make the attractant.

To produce the attractant 14 one mixes human urine 10 with the urine of the animal 12. One uses the human urine 10 as the base since it is cheaper and easier to obtain. In the preferred embodiment applicant uses male human urine 10. However he could also use female urine or female urine during menstruation or any combination thereof. One ages the urine for two or three days. In the preferred embodiment one mixes approximately fifteen parts human urine 10 with one or two parts animal urine 12 as shown in FIG. 1. As in the case of human urine 10 one can use animal urine 12 from male, female or the female during heat. One can also obtain animal urine 12 both natural and synthetic. In the preferred embodiment synthetic urine is used since it has a longer shelf life.

To produce the preferred embodiment for an attractant 14 for deer hunting, one begins by collecting human urine 10 and in the preferred embodiment, male human urine and allows it to age for two to three days. One could also uses female urine or urine from a female during menstruation. He then mixes approximately fourteen to fifteen parts of the human urine 10 that has been aged two or three days with the one or two parts of animal urine 12. In the preferred embodiment he uses synthetic dominant male urine 12. However, he could use female urine, natural or synthetic or natural animal urine. The advantage of using synthetic urine is that it does not break down as quickly as the natural urines. This makes up the liquid to create the scent.

When one goes out hunting one takes along large quantities of the attractant 14. In the case of deer hunting one takes along approximately sixteen ounces of attractant 14. This large amount of attractant 14 is necessary for this scent to work effectively. Applicant has found that using smaller amounts of scenting material does not attract the animals. He found this to be not only true about the attractant 14 of this patent but also about most of the commercial scenting materials now on the market.

Figure 2:
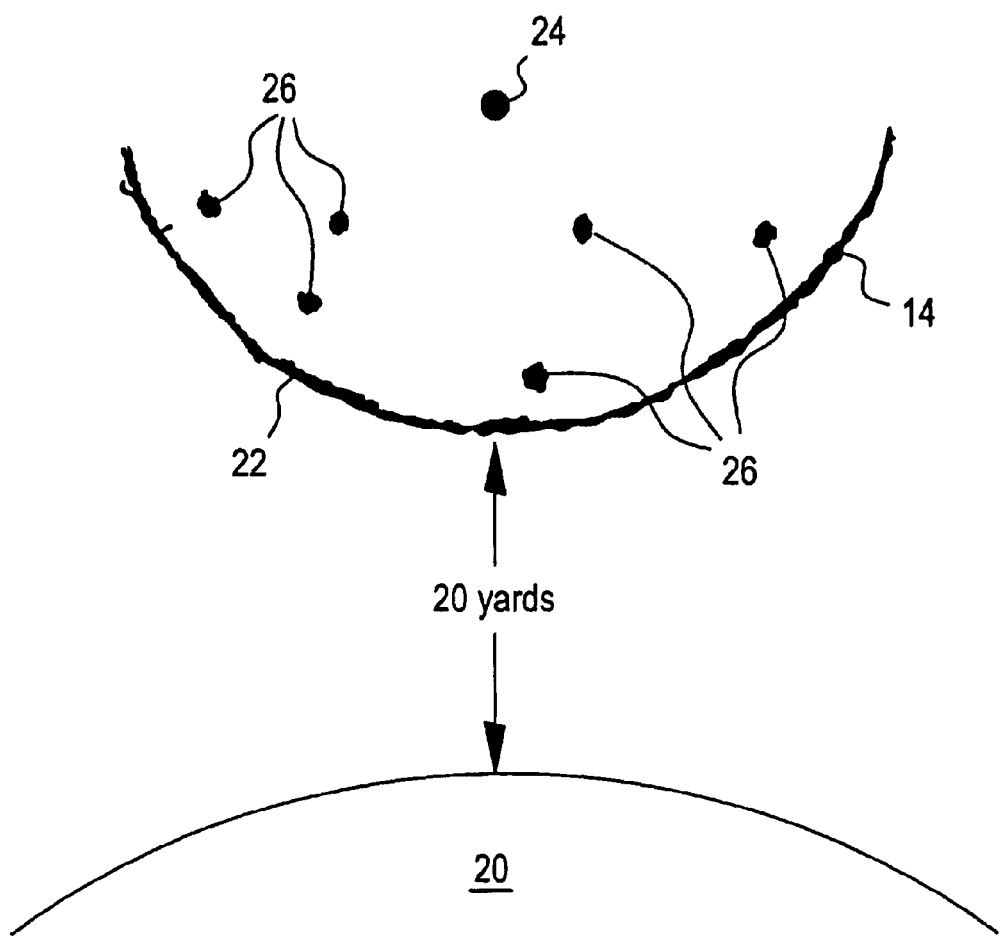
FIG. 2 show how the attractant is placed at the hunting site.

FIG. 2 shows how the attractant 14 is placed to attract animals. One first tries to get close to the animals bedding area 20, the place where the animal sleeps. If possible one tries to get with twenty years of the bedding area 20. One must place the attractant 14 up wind from the animals bedding area 20 in order for the animals to pick up the smell. This means that one must have good scent elimination for oneself or the animals will smell him/her.

One than pours the attractant 14 in a semicircle 22 approximately twenty yards from the stand 24 or one's hiding place. One pours the attractant 10 on deadfalls, letting it stream down trees. One also pours the mixture on any scrapes 26. Scrapes 26 are places on the ground that male animals have pawed and then the male animals urinate on these areas to attract females for breeding. If there are no scrapes 26, one clears away some of the ground with his boot and pours the scenting mixture on the cleared ground.

For deer the attractant can also be used in combination with soft deer calling, rattling horns and grunt tube.

The attractant 14 can be stored for periods of over a month by adding a tablespoon of either ammonia or bleach to kill the bacteria to each gallon of the attractant 10.

What is claimed is:

1. An animal attractant comprising:
 a. human urine; and,
 b. animal urine;
 c. the animal and human urine is mixed in the ratio of seven or more parts human urine with one part animal urine.

2. An animal attractant as in claim 1 wherein:
 a. the human urine has been aged for at least two days.

3. An animal attractant as in claim 1 wherein:
 a. the animal urine is synthetic animal urine.

4. An animal attractant as in claim 1 wherein:
 a. the animal urine is from a male deer.

5. An animal attractant as in claim 1 wherein;
 a. the animal urine is synthetic male deer urine.

6. An animal attractant as in claim 1 further comprising:
 a. whereas the animal attractant contains human urine and animal urine in the ratio 15 parts human urine to 1 part animal urine.

7. An animal attractant as in claim 1 further comprising:
 a. whereas the animal attractant contains human urine and animal urine in the ratio 14 parts human urine to one part animal urine.

8. An animal attractant as in claim 1 further comprising:
 a. whereas the animal attractant contains human urine and animal urine in the ratio of 15 parts human urine to 2 parts animal urine.

9. An animal attractant as in claim 1 further comprising:
 a, whereas the animal attractant contains animal urine and human urine in the ratio of 14 parts human urine to 2 parts animal urine.

10. An animal attractant as in claim 1 further comprising:
 a. ammonia.

11. An animal attractant as in claim 10 wherein:
 a. the amount of ammonia added to the mixture human urine and animal urine per 1 gallon of mixture is 1 teaspoon.

12. An animal attractant as in claim 1 further comprising;
 a. bleach.

13. An animal attractant as in claim 12 wherein:
 a. the amount of bleach added to the mixture of human urine and animal urine per 1 gallon of mixture is 1 teaspoon.

14. An animal attractant prepared by a process comprising the steps of:
 a. obtaining human urine; and,
 b. obtaining animal urine; and,
 c. mixing human urine with animal urine in the ratio of seven or more parts human urine with one part animal urine.

15. An animal attractant prepared by the process as in claim 14 wherein:
 a. the human urine and animal is mixed in the ratio of 14 parts human urine to 1 part animal urine.

16. An animal attractant prepared by the process comprising:
 a. obtaining human urine; and,
 b. obtaining animal urine; and,
 c. mixing human urine with animal urine; and.
 d. adding an agent to kill the bacteria.

17. An animal attractant prepared by the process as in claim 16 wherein:
 a. the agent that kills bacteria is ammonia.

18. An animal attractant prepared by the process as in claim 17 wherein:
 a. one teaspoon of ammonia is added for each gallon of attractant.

19. An animal attractant prepared by the process as in claim 16 wherein:
 a. the agent that kills bacteria is bleach.

20. An animal attractant prepared by the process as in claim 19 wherein:
 a. 1 teaspoon of bleach is added to each gallon of attractant.

* * * * *